United States Patent [19]

Harris et al.

[11] 4,021,370

[45] May 3, 1977

[54] FUEL GAS PRODUCTION

[75] Inventors: Norman Harris; Thomas Frederick Shevels, both of Stockton-On-Tees; Alan James Dennis, Middlesborough, all of England

[73] Assignee: Davy Powergas Limited, England

[22] Filed: Oct. 17, 1975

[21] Appl. No.: 623,503

Related U.S. Application Data

[63] Continuation-in-part of Ser. No. 485,625, July 3, 1974, abandoned.

[30] Foreign Application Priority Data

July 24, 1973 United Kingdom ............ 35130/73
July 24, 1973 United Kingdom ............ 35132/73

[52] U.S. Cl. .............................. 252/437; 252/465; 252/470; 48/197 R
[51] Int. Cl.$^2$ ..................... B01J 27/18; B01J 23/86
[58] Field of Search ................. 252/437, 465, 470

[56] References Cited

UNITED STATES PATENTS

| | | | |
|---|---|---|---|
| 2,600,655 | 6/1952 | Jacobs et al. ...................... | 252/470 |
| 2,658,858 | 11/1953 | Lane et al. ...................... | 252/470 X |
| 3,327,006 | 6/1967 | Noddings et al. .............. | 252/437X |
| 3,485,882 | 12/1969 | Hess et al. ...................... | 252/465 X |

*Primary Examiner*—Patrick P. Garvin
*Attorney, Agent, or Firm*—Morton, Bernard, Brown, Roberts & Sutherland

[57] ABSTRACT

A process is described for the production of methane from methanol by catalytic dehydration and dehydrogenation providing a high initial methane yield and a final substitute natural gas product of high calorific value. The catalytic dehydration and dehydrogenation steps may be effected simultaneously or in sequence. High efficiency in usage of raw materials and thermal requirements of the process are secured. A preferred catalyst containing both dehydration and dehydrogenation functions consists essentially of a major amount of iron oxide and minor amounts of chromium oxide and phosphate or tungstate ions.

14 Claims, No Drawings

FUEL GAS PRODUCTION

This application is a continuation-in-part of our co-pending U.S. Pat. application Ser. No. 485,625, filed 3rd July 1974 abandoned.

This invention relates to catalytic processes for the gasification of methanol as used for the production of methane from methanol.

Methanol can be gasified in the presence of steam, using a metal catalyst, for example a nickel catalyst, and a temperature of less than 400° C, according to the exothermic reaction $$4CH_3OH \rightarrow 3CH_4 + CO_2 + 2H_2O \tag{1}$$

At high concentrations of methanol, the methanol is initially converted to carbon monoxide and hydrogen according to the equation: $CH_3OH \rightleftharpoons CO + 2H_2$; (2)

which reaction is endothermic.

Subsequent exotheric reactions to produce methane and carbon dioxide according to the following equations $$CO + 3H_2 \rightleftharpoons CH_4 + H_2O \tag{3}$$
$$CO + H_2O \rightleftharpoons CO_2 + H_2 \tag{4}$$

are inhibited by the high concentration of methanol, but as the methanol is converted, its concentration is reduced, thereby permitting these reactions to take place. In a continuous flow reactor there is the danger of the reaction quenching itself because the initial reaction at high concentration of methanol (equation 2) is endothermic which tends to produce an initial decrease in temperature at the inlet of the reactor. There is a further disadvantage that there is a danger of carbon being deposited, before reactions 3 and 4 take place, according to the equations $$CO + H_2 \rightarrow C + H_2O \tag{5}$$

$$2CO \rightleftharpoons C + CO_2. \tag{6}$$

It is an object of the present invention to provide a process for the production of methane from methanol which can be effected continuously without danger of the reaction quenching itself.

It is a further object of the invention to provide a process for the production of methane from methanol in which deposition of carbon on the catalyst is substantially prevented.

It is a still further object of he invention to provide a single stage process for the production of methane in high yield from methanol.

It is yet a further object of the invention to provide a modified CRG process (catalytic rich gas process) enabling the use therein of methanol as a feedstock.

Another object of the invention is to provide a modified form of the CRG hydrogasification process using methanol as a feedstock in partial replacement of naphtha or LPG (liquefied petroleum gas).

It is yet another object of the present invention to provide a process for converting methanol to methane in which a significant amount of the carbon in the feedstock appears as methane produced by a route other than carbon oxide reduction.

The present invention utilises as catalysts for the decomposition of methanol, either simultaneously or in sequence, catalytic materials incorporating dehydration and dehydrogenation functions so that the methanol is decomposed according to a mechanism such that not all of it needs first to be broken down to carbon oxides and hydrogen. With catalysts incorporating these characteristics we believe that a significant amount of methane is produced by a mechanism other than by the hydrogenation of carbon oxides. In other words, we believe that at least 5% of the carbon in the feedstock appears as methane produced by a route other than carbon oxide reduction.

A first preferred mode of operation involves contacting a feed comprising methanol vapour with a solid dehydration catalyst. It is believed that at least part of the methanol is converted to dimethyl ether. The intermediate reaction product is contacted with a dehydrogenation catalyst to produce methane, apparently by converting at least part of the dimethyl ether to methane. The reactions which are apparently involved are:

$$2CH_3OH \rightarrow CH_3OCH_3 + H_2O \tag{7}$$

$$CH_3OCH_3 + H_2O \rightarrow CH_4 + CO_2 + 2H_2 \tag{8}$$

The overall reaction can thus be expressed as:

$$2CH_3OH \rightarrow CH_4 + CO_2 + 2H_2 \tag{9}$$

It will be seen by these equations that 50% of the carbon initially present in the methanol appears as methane. In other words, the selectivity of the overall reaction to methane may be up to 50%.

(The term "selectivity" is defined as $$\frac{\% \text{ by volume methane}}{(\% \text{ by volume methane} + \% \text{ by volume carbon oxides})} \times 100$$

all gas volumes being measured on a dry basis).

Examples of suitable solid dehydration catalysts include metal phosphates and metal tungstates such as aluminum phosphate, ferric phosphate, chromium phosphate, aluminum tungstate, ferric tungstate and chromium tungstate, and refractory oxides such as alumina, and silica; and mixtures thereof.

Examples of suitable dehydrogenation catalysts include metal oxides such as copper oxide, zinc oxide, iron oxide/chromium oxide mixtures; Group 8 metals (e.g. nickel), metallic copper; and mixtures thereof.

In the case of metal catalysts these are usually conveniently supported on a refractory oxide support such as silica or alumina. The oxide catalysts may be similarly supported but may also be used in an unsupported form.

In this first mode of operation the feed is reacted by contact with the solid dehydration catalyst, at dehydration conditions, for instance, at a temperature of from about 150° to about 750° C, preferably from about 200° C to about 650° C, and at a pressure of from about 0 psig up to about 3000 psia, but preferably not exceeding 2000 psig. Particularly preferred reaction conditions are from about 300° C to about 550° C and from about 150 psia to about 1200 psia. In the second stage of this mode of operation, dehydrogenation conditions are maintained, and the temperature and pressure ranges maintained over the dehydrogenation catalyst are preferably similar to those recited for the dehydration reaction.

In this first mode of operation it is possible to effect the process in the absence of steam. However it will usually be preferred to operate both the dehydration and the dehydrogenation in the presence of steam. Thus it is preferred to use a feed comprising steam and methanol vapour in a molar ratio of steam to methanol of from about 0.2:1 to about 10:1, preferably about 2:1 or less. A convenient feed comprises an approximately 1:1 molar ratio steam/methanol vapour feed.

A second preferred mode of operation involves contacting a feed comprising methanol vapour with a catalyst composition containing simultaneously dehydration and dehydrogenation functions. Examples of such catalyst compositions include mixtures of at least one of the dehydration catalysts mentioned hereinabove and at least one of the dehydrogenation catalysts (other than Group 8 metals) listed hereinabove. A particularly preferred composition containing both dehydration and dehydrogenation functions comprises a mixed iron and chromium oxides modified by incorporation of chemically combined phosphate or tungstate ions in a minor amount sufficient to impart a dehydration function to the composition. The proportion of chromium may be a minor amount that is catalytically effective and is sufficient to impart physical stability to the catalyst under the reaction conditions to be employed more particularly to prevent sintering of the catalyst particles for example at least about 4% e.g. in the range of from about 4 to about 20% by weight calculated as chromium oxide ($Cr_2O_3$). Typically such compositions include about 0.5 to about 10 weight % of total phosphate and tungstate ions. For example, the catalyst may contain at least about 0.5% up to about 9% or to about 10% by weight of phosphate ions, preferably up to about 9% by weight, e.g., about 1% to about 9% by weight, or from about 0.5% to about 10% by weight of tungstate ions. Particularly preferred compositions include those containing at least about 6% by weight of chromium, preferably about 8% to about 18% by weight of chromium, calculated as chromium oxide ($Cr_2O_3$). Iron oxides generally comprise the major proportion of the catalyst and may be the essential balance, although other materials may be present. Thus, the iron may often comprise about 70 to about 95% by weight of the catalyst, preferably about 80 to about 90 weight percent, calculated as $Fe_2O_3$. The iron and chromium oxides may be present in their various forms, and the amounts of those oxides and phosphate or tungstate ions are based on their total weight present. The catalyst may be on a support, e.g. a refractory oxide such as silica or alumina, and the foregoing amounts are based on the total of the iron and chromium oxides and phosphate and tungstate ions.

Group 8 metals, such as nickel, can act as dehydrogenation catalysts but are best avoided in the catalyst composition used in the second preferred mode of operation for gasification of methanol because of the above-mentioned disadvantages, particularly the danger of the reaction quenching. (However, as will appear below, Group 8 metal catalysts can be used in subsequent reaction steps).

In this second preferred mode of operation the feed may comprise, in addition to the methanol vapour, steam in an amount corresponding to a molar steam: methanol ratio of from about 0.2:1 to about 10:1, preferably not more than about 2:1 and conveniently about 1:1

The presence of steam is important with the use of an oxide catalyst, for example a mixed iron oxide/ chromium oxide catalyst, which has been treated with a material such as phosphoric acid to impart a dehydration function to the catalyst, since the steam will ensure that the oxide catalysts are not reduced to metallic form. The preferred catalyst composition for use in this second mode of operation is conveniently prepared by coprecipitation of mixed iron and chromium oxides, followed by incorporation of the dehydration catalytic material and calcination. Thus, for example, a solution of a ferrous salt (e.g. ferrous sulphate can be added to an alkaline dichromate solution (e.g. an aqueous solution containing sodium or potassium carbonate and sodium or potassium dichromate) to cause precipitation of the mixed oxides according to the reaction:

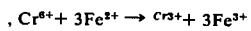
$Cr^{6+} + 3Fe^{2+} \rightarrow Cr^{3+} + 3Fe^{3+}$

As will be appreciated this reaction sets an upper limit on the chromium content of the mixed oxides of 23.69 percent by weight calculated as chromium oxide. By varying the proportions of dichromate and ferrous ions varying proportions of chromium can be incorporated in the mixed iron-chromium oxide precipitate. Generally speaking, we prefer to incorporate at least about 4 percent by weight up to about 20 percent by weight, and preferably from about 8 percent to about 18 percent by weight, of chromium calculated as chromium oxide in the precipitate.

The precipitate is then collected and mixed with the dehydration catalyst. Thus one precedure involves physical admixture in the desired proportions of the iron oxide/chromium oxide precipitate and of the chosen dehydration catalytic material. Alternatively the precipitate is treated with a suitable modifying agent such as phosphoric acid or tungstic acid so as to incorporate in the composition the desired dehydration catalytic material.

According to one precedure the precipitated mixed iron-chromium oxides are treated with an aqueous solution of phosphoric acid or tungstic acid and the treated precipitate is calcined. In a varient of this procedure the mixed iron-chromium oxides are treated with an aqueous solution of a water-soluble phosphate or tungstate, e.g. sodium or potassium phosphate or tungstate, and then washed to remove the water-soluble sodium or potassium cations before calcination.

According to another procedure the mixed iron-chromium oxides are mixed with the dehydration catalyst, e.g. aluminum phosphate, aluminum tungstate, silica or gamma-alumina, and then calcined.

The proportion of dehydration catalyst added to or incorporated in the mixed iron-chromium oxides varies according to the catalytic activity of the dehydration catalyst. Thus, for example, when using an activated alumina as the added dehydration catalyst, it will usually be desirable to incorporate at least about 10 percent by weight of alumina up to 70 percent by weight or more. When the added dehydration catalyst is a tungstate e.g. ferric or chromium or aluminum tungstate, it is usual to incorporate from about 0.5 percent by weight up to about 10 percent by weight or more. Aluminium phosphate is desirably incorporated in a proportion of from about 0.5 percent by weight up to about 20 percent by weight or more. When treating a mixed iron-chromium oxide precipitate with phosphoric acid it is preferred to use a quantity corresponding to from about 0.5 to about 9 percent (preferably about 1 to about 9 percent) by weight calculated as phosphate ions. Mixtures of two or more such dehydration catalysts may be incorporated in the mixed iron-chromium oxide catalyst.

We believe that the mechanism of the decomposition of methanol over a catalyst comprising metal oxides, such as iron/chromium oxide mixtures, is completely different from that outlined above relating to the use of Group 8 metal catalysts in metallic form. We have shown using such oxide catalysts that a primary decomposition product of methanol is methane, the selectivity to methane being independent of methanol converted. For example, using a typical high temperature shift catalyst comprising a mixture of iron oxide and chromium oxide at a temperature of 450° C., 600 psig and a steam ratio of 3:1, the selectivity to methane was found to be 15%. The addition to the catalyst of 5% by weight phosphate ions by reaction of the mixed oxides with phosphoric acid following by calcination imparts a dehydration function to the catalyst and is found under similar reaction conditions to give a selectivity of 32%. By use of a suitable phosphate modified mixed iron and chromium oxide catalyst under suitable conditions we have been able to achieve selectivities of up to 50%, i.e the maximum figure allowed by equation (9) above. We believe that using such a catalyst substantially all of the methane is produced from methanol in the second preferred mode of operation by the sequence of reactions (7) and (8), which are summarised as equation (9) above.

The proportion of methane in the primary decomposition products is dependent at least in part on the relative dehydration/dehydrogenation activities of the metal oxide catalyst which in turn are functions of the chemical constitution of the catalyst. With metal oxide catalysts of low dehydration activity which produce low proportions of methane in the primary decomposition products the primary decomposition reaction is endothermic. However with increasing methane content consequent upon increased dehydration activity of the catalyst the endothermicity of the primary decomposition reaction decreases until, at a methane selectivity of about 37% in the primary decomposition products the overall reaction becomes thermally neutral. Above these methane levels the catalytic primary decomposition reaction of methanol becomes exothermic. As shown in the Examples below it is possible using appropriate phosphate-modified iron/chromium oxide catalyst mixtures to achieve methane selectivities as high as 50%.

In a preferred form of operation a catalyst combining dehydration and dehydrogenation functions is employed in a first stage, and a second stage of the process consists of conventional catalytic methanation using a normal methanation catalyst, typically a Group 8 metal, for example a nickel catalyst such as a nickel on alumina catalyst.

Among advantages achieved by such a process are: 1. The methane produced by decomposition of methanol in the first stage results in the reduction of the endothermicity of the primary decomposition reaction so that the risk of chilling of the catalyst is reduced and can be eliminated by correct catalyst selection.

2. The risk of carbon deposition is reduced.

3. Since the product of the first stage has a significant methane content the methanation duty of the subsequent stages and the associated necessity for any heat removal is reduced.

The amount of methane in the primary decomposition products from the first stage of such a process is an important factor, for the reasons:

a. as the methane content of the primary decomposition product gases increases the endothermicity of the reaction decreases and at about 37% methane in the existing gas the reaction becomes thermally neutral and above this level is exothermic; and b. the heat removal duty and the methanation duty in the second stage of the process is significantly reduced as the methane concentration from the first stage increases.

Preferably the present process for the catalytic gasification of methanol with the use of catalytic materials incorporating dehydration and dehydrogenation functions is effected in a manner such that the methane produced in a primary gasification stage exceeds about 30% on a selectivity basis, and more preferably exceeds about 37 or 40%. The desired goal is 50% methane on a selectivity basis and clearly the nearer the methane content is to achieving this figure the better.

In a simple form the process may comprise the reaction over a first stage catalyst (i.e. dehydration catalyst or a catalyst possessing both dehydration and dehydrogenation functions) followed by a methanation stage and these two stages may be repeated. Alternatively however more than one stage of each type of catalyst treatment may be used, i.e. when for example a first stage catalyst is used such that the decomposition of methanol in a first stage is exothermic, the temperature may be modified by injecting further methanol between successive beds of catalyst or stages of the same catalytic treatment. Subsequent methanation may be carried out in the conventional fashion. Appropriate adjustment of the steam content may be effected as well as temperature control when additional methanol is injected. The thermal efficiency of the multi-stage process is higher than that of the simple two-stage process since smaller amounts of steam need to be added to the reactants and use is made of the heat of reaction to vapourize and pre-heat the methanol, particularly when the first stage is itself exothermic with the production of more than about 37% of methane on a selectivity basis.

As already mentioned, it is also possible to carry out the functions of dehydration and dehydrogenation separately rather than incorporate the two functions into a single catalyst. It is thus possible for example to decompose methanol over a dehydration catalyst as referred to above (for example aluminum phosphate) and pass the product either over a dehydrogenation catalyst as referred to above and preferably followed by methanation, or alternatively directly to a catalyst incorporating both of the dehydrogenation and methanation functions for example a Group 8 metal such a nickel. Thus methanol may first be dehydrated to dimethyl ether with the use of aluminium phosphate as a dehydration catalyst, and the product treated further with mixed iron and chromium oxide catalyst or with a nickel catalyst direct. The mixed oxide catalyst treatment may be followed by a final methanation over a nickel catalyst.

It is of advantage to employ at any stage of the present process a reaction chamber in which there is maintained a fluidised bed of catalyst material, so as to promote heat transfer between the reactants. When using a fluidised bed the catalyst material is preferably of microspheroidal form. It is of particular value to employ a fluidised catalyst bed in the primary methanol gasification stage. The pressure of the vapour supply of methanol and steam may be employed to fluidise the catalyst bed in a chamber to which water may be supplied for temperature control and which may have a dust extracting device in the offtake line. With a fluidised catalyst bed pre-heating of the reactants (such as methanol) may be reduced or obviated and carbon deposit in the catalyst is reduced or avoided.

When a final methanation stage over a nickel catalyst is included in the process, then an added feedstock of L.P.G. (liquefied petroleum gas) or naphtha may be used at this stage by injection into the products of methanol gasification. Introduction of this added feedstock can secure increased efficiency in terms of product conversion, that is a better usage of the carbon content of the L.P.G. or naphtha and consequently a lower carbon dioxide removal requirement later in the process for a given quantity of methane. L.P.G.consists of a mixture of low boiling hydrocarbons (predominantly $C_1$ to $C_5$ hydrocarbons) and can be converted to methane in the presence of a methanation catalyst by reaction with steam, for example, as follows:

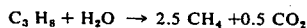
$$C_3H_8 + H_2O \rightarrow 2.5\, CH_4 + 0.5\, CO_2$$

This reaction is mildly exothermic and much less exothermic than conventional methanation of carbon oxides. Thus the injection of LPG or naphtha into the products of methanol gasification can be used to moderate the temperature rise across the methanator which reduces the duty load on the methanator An increased output of methane can thus be secured from a methanol gasification plant of a given size by addition of a facility for injection of L.P.G. or naphtha before the methanation stage and such combined plant is also adaptable for usage according to availability of feedstock.

Thus a known process for the production of methane from naphtha or L.P.G., the CRG process or rather a modified form of such process known as the CRG hydrogasification process, may readily be modified in accordance with the present invention so as to use a methanol feedstock in partial replacement of LPG or naphtha. In the CRG process a hydrocarbon feedstock (such as LPG or naphtha) is blended with steam and is reacted over a nickel catalyst in an adiabatic reactor. The product gases are at equilibrium for the methane/-steam reaction (reaction 3 above) and the water gas shift reaction (reaction 4 above) and are normally treated further for the methanation of the oxides of carbon using a nickel methanation catalyst, followed by removal of carbon dioxide, to produce a substitute natural gas. In the hydrogasification modification, part of the hydrocarbon is injected after the first stage adiabatic reactor and further methanation and $CO_2$ removal effected. Methanol cannot normally be used as a feedstock in the CRG or hydrogasification processes since it inhibits a nickel catalyst from methanating oxides of carbon and the rate of decomposition of methanol to carbon monoxide and hydrogen is much greater than the rate of methanation of carbon monoxide with hydrogen to produce methane. If the nickel catalyst of the first stage is replaced in a CRG/hydrogasification process by, for example, a phosphatemodified mixed iron and chromium oxide catalyst of the type described above, a methanol feedstock can be employed to provide a high methane content at this stage. Injection of naphtha into the gaseous product from the first stage followed by hydrogasification, subsequent methanation and $CO_2$ removal in later stages of the plant provides a substitute natural gas of high chlorific value, for example of greater than 900 B th U per standard cubic foot of gas (dry).

The methane-containing product gas obtained in accordance with the invention by contacting a feed comprising methanol vapour simultaneously or in sequence with a dehydration catalyst and with a dehydrogenation catalyst can be used as a standby feedstock for a steam reformer of a conventional hydrogen plant. Such a steam reformer normally operates on a hydrocarbon feedstock, such as natural gas or another source of methane to produce a mixture of carbon monoxide and hydrogen. In the case of methane this proceeds by the reverse reaction of equation (3) above. In the hydrogen plant the steam reformer is succeeded by downstream CO-shift and $CO_2$-removal stages. In the CO-shift stage CO is converted to $CO_2$ and further hydrogen produced by equation (4) above. Essentially pure hydrogen results from the $CO_2$ removal stage. In the modification of such a hydrogen plant to use methanol as a standby feedstock it is merely necessary to provide a standby reactor containing, for example, the phosphatemodified mixed iron oxide/chromium oxide catalyst described above. This standby reactor is connected to the steam reformer by means of a standby connection and is provided with a suitable methanol feed arrangement.

The invention is illustrated further with reference to the following Examples.

EXAMPLE 1

A methanol gasification catalyst was prepared by co-precipitating $Fe_2O_3/Cr_2O_3$ oxides from mixed solutions of ferrous sulphate and potassium dichromate with a solution of sodium carbonate. The ratio of ferrous sulphate to potassium dichromate was adjusted to give a binary $Fe_2O_3/Cr_2O_3$ mixture containing 8% by weight of $Cr_2O_3$. This binary oxide mixture was washed with water to remove sulphate. The cake was then dried for 4 hours at 300° C.

The dried cake was crushed to a powder and added to a solution of dilute phosphoric acid ($H_3PO_4$); the strength of the acid was equivalent to 2% $PO_4^{-3}$ by weight of the binary oxide mixture. The slurry was stirred for one hour and the solid filtered off and again dried at 300° C. Chemicalanalysis of the solid showed that it had reacted with all the phosphate as the solid contained 2% $PO_4^{-3}$, confirmed by analysis of the filtrate which contained no phosphate.

The dried powder was mixed with 2% graphite and pelletted as 3/16 × 3/16 tablets. 120 mils of the tablets were charged to an experimental adiabatic methanol gasification reactor. The catalyst was reduced for 24 hours in $H_2O/H_2$(1:1) during which time the $H_2S$ level in the exit gas dropped below 0.1 parts per million. Into three separate similar adiabatic reactors were charged 80 mls each of Girdler's G.87 methanation catalyst (a conventional nickel-on-alumina catalyst). The three methanation reactors were connected in series with the reactor containing the gasification catalyst, giving a total of four catalyst beds in series. The three methanators were reduced with $H_2O/H_2$ (1:1) for 24 hours at 350° C before all reactors were linked together. The inlet temperature to each reactor was controlled by preheating in a molten salt bath.

625 mls/hour of methanol/water (1:1 molar) were pumped to the gasifier preheater where vapourization occurred and the inlet temperature to the methanol gasification catalyst adjusted to 420° C. The salt baths at the methanator inlets were adjusted to give an inlet temperature of 315° C at all bed inlets. The pressure of the four reactors was controlled at 120° psia.

The temperature rise across the gasifier was measured as 185° C and this remained constant during 1,000 hours continuous operation. Thermochemical calculation shows that this temperature increase is equivalent to 50% of the methanol being converted to methane. Every twelve hours during the 1,000 hours run the temperature profile was measured, providing an indication of catalyst activity, and the selectivity to $CH_4$ was determined. After the initial bedding in period of 100 hours no significant changes in activity or selectivity were observed. No deposition of carbon on the catalyst was apparent.

Temperature profiles were measured in the three methanators in a similar fashion and again no significant change in activity was noted after the initial 100 hours. Gas analysis and exit temperature measurement showed that the gas was at equilibrium at the exit of each methanation reactor for the reactions:

$$CO + 3H_2 \rightleftharpoons CH_4 + H_2O$$

$$CO + H_2O \rightleftharpoons CO_2 + H_2$$

The exit gas from the final reactor was passed through a sodium hydroxide scrubber to remove $CO_2$ down to less than 0.1% and analysis of the product, a synthetic or substitute natural gas, showed the gas to have a calorific valve of 984 B.Th.U. per standard cubic foot (dry).

The experimental reactors each consisted of a 1 inch internal diameter tube a part of which was surrounded by an outer metal casing sealed at the base. The metal casing was filled with vermiculite as an insulating material and the inlet to the catalyst bed was located just above the lowermost level of the insulation. The reactor was immersed in a bath of molten salt, and reaction conditions in the insulated reactor were substantially adiabatic in nature. From inlet and exit gas analyses and temperature measurement it was possible to calculate the temperature which would be achieved in a true adiabatic reactor. The inlet tube to the base of the reactor passed down through the salt bath and secured vapourization of premixed methanol and water pumped to the reactor during use.

Examples 2 to 9

In these examples the mixed oxide catalyst was prepared by dissolving appropriate quantities first of $FeSO_4 \cdot 7H_2O$ and secondly of $Na_2Cr_2O_7 \cdot 2H_2O$, $Na_3PO_4$, and $Na_2CO_3$ in roughly equal quantities of water and adjusting the temperature of the solutions to 80° C. The mixed solution was added over 45 minutes to the ferrous sulphate solution during continuous stirring while maintaining the temperature at 80° C. The precipitate was filtered, calcined at 300° C, crushed to less than 12 mesh (B.S.S.) size and washed. The granules were dried at 110° C, mixed with 2% by weight of graphite and pelleted as ¼ inch by ¼ tablets.

The catalyst compositions were varied for different examples but for Examples 3 and 8 there was employed as starting materials:

| | | |
|---|---|---|
| $Na_3PO_4$ | 11.4 grams | |
| $Na_2Cr_2O_7 \cdot 2H_2O$ | 114.0 grams | $FeSO_4 \cdot 7H_2O$ 833.0 grams |
| $Na_2CO_3$ | 270.0 grams | |

The ferrous sulphate was dissolved in 4 litres of water and the other constituents dissolved in 3 litres of water before adjusting the temperatures and mixing. The target and actual compositions of the catalyst were:

| | | | | |
|---|---|---|---|---|
| $Cr_2O_3$ | Target | 17.5% | Actual | 16.6% |
| $PO_4^{3-}$ | | 2.0% | | 2.03% |

The catalysts for the different examples were charged to the experimental reactor immersed in a molten salt bath and some examples carried out without the vermiculite insulation container so as to give isothermal conditions controlled by the temperature of the salt bath.

Methanol and water were premixed to a desired composition and the mixture pumped to the reactor at a selected pressure. The following results were obtained, as given in Table 1, the conditions applied in each case also being given in the table.

TABLE 1

| Example No. | Catalyst % $Cr_2O_3$ | % $PO_4^{3-}$ | Reaction condition | Inlet Temperature | Pressure psia | $H_2O$/MeOH Molar ratio | % selectivity to methane | Temperature increase ° C |
|---|---|---|---|---|---|---|---|---|
| 2 | 8.8 | 4.5 | Isothermal | 475 | 600 | 1:1 | 45.0 | +115* |
| 3 | 16.6 | 2.03 | Isothermal | 475 | 1200 | 1:1 | 46.0 | +130* |
| 4 | 12.3 | 8.1 | Isothermal | 475 | 1200 | 1:1 | 45.6 | +120* |
| 5 | 15.4 | 7.9 | Isothermal | 475 | 1200 | 1:1 | 43.0 | + 85* |
| 6 | 14.7 | 2.4 | Isothermal | 475 | 1200 | 1:1 | 42.0 | + 75* |
| 7 | 14.7 | 2.4 | Isothermal | 475 | 1200 | 1:2 | 45.1 | +120* |
| 8 | 16.6 | 2.03 | Adiabatic | 450 | 1200 | 1:2 | 49.0 | +190** |
| 9 | 16.5 | 2.03 | Adiabatic | 450 | 600 | 1:2 | 47.0 | +150** |

*calculated
**observed

All selectivities are based on 100% conversion of methanol and are calculated from dry gas analyses, using the basis $$\% \text{ selectivity} = \frac{\% \text{ methane}}{\% \text{ methane} + \% \text{ carbon oxides}} \times 100$$

In the isothermal reactors the catalyst volumes were 20 mls and in the adiabatic reactors were 60 mls. In all cases the space velocity was 2000 $Hr^{-1}$ based on the gas flow of methanol.

EXAMPLES 10 to 13

In these examples catalyst compositions were prepared by the method given in Example 1 but with variation of the chromium oxide content. The catalysts were charged to the experimental reactor and a methanol and water mixture pumped through the reactor while immersed in a molten salt bath. Conditions of treatment and results secured in these Examples are given in Table 2.

TABLE 2

| Example No. | Catalyst % $Cr_2O_3$ | % $PO_4^{3-}$ | Reaction conditions | Inlet Temperature | Pressure psia | $H_2O$/MeOH molar ratio | % selectivity to methane |
|---|---|---|---|---|---|---|---|
| 10 | 17.5 | 2.3 | Isothermal | 475 | 600 | 1:1 | 43.2 |
| 11 | 17.5% | 2.3 | Isothermal | 475 | 1000 | 1:1 | 45.1 |
| 12 | 8.0 | 1.8 | Adiabatic | 450 | 1000 | 1:1 | 50 |
| 13 | 8.0 | 1.3 | Adiabatic | 450 | 1000 | 1:1 | 50 |

EXAMPLE 14

A modified form of a commercially available $Fe_2O_3/CR_2O_3$ (8% by weight of Cr content calculated as $Cr_2O_3$) manufactured by Girdler Chemicals Inc., Louisville, Ky. was used in this Example. During manufacture the catalyst had been modified by incorporation of phosphate ions by treatment with phosphoric acid prior to calcining and drying. Analysis showed the phosphate content to be 2% by weight.

The catalyst was charged to the experimental reactor of Examples 1 to 13 and a mixture of methanol vapour and steam (1:1 molar ratio) was passed at atmospheric pressure through the reactor which was immersed in a salt bath. The inlet temperature was 400° C and the gas space velocity (based on methanol) was 2000 $hr^{-1}$. The methanol was totally converted to methane, carbon oxides and hydrogen. The selectivity to methane was 50%.

After an initial bedding-in period the activity of the catalyst remained unchanged trhoughout 1000 hours of continuous operation.

EXAMPLE 15

The procedure of Example 14 was repeated using a similarly manufactured catalyst with a 1% by weight phosphate content. Similarly good results were obtained.

EXAMPLE 16

Equally good results are obtained using in place of the catalyst of Example 14 a similarly manufactured catalyst with a 4% by weight phosphate content.

EXAMPLE 17

The procedure of Example 15 was repeated except that the operating pressure was increased to 400 psia. Similarly good results were obtained.

EXAMPLE 18

Example 17 was repeated except that the operating pressure was decreased to 200 psia. Good results were again obtained, in particular (as also in each of Examples 15 to 17) the selectivity to methane was 50%.

EXAMPLE 19

This example shows the use of a two-stage procedure. In this case two experimental reactors were used in series, each immersed in a molten salt bath heated to the appropriate temperature.

The primary stage reactor was charged with ¼ inch aluminium phosphate pellets (formed by pelletizing aluminum phosphate powder using "Sterotex" as a binding agent). The secondary stage reactor was charged with a normal high temperature shift catalyst (Girdler G3 catalyst). This had an 8% by weight chromium content, calculated as $Cr_2O_3$, and was essentially phosphate-free.

The primary stage reactor was fed with a methanol/steam mixture (1:1 molar ratio), the inlet temperature being 400° C. The gas space velocity (based on methanol) was 2000$hr^{-1}$ and the pressure was 400 psia. Analysis of the exit gases from the primary stage reactor indicated that the methanol had been converted quantitatively to dimethyl ether.

The exit gases from the primary stage reactor were passed to the inlet of the secondary stage reactor which was also maintained at 400° C. Analysis of the exit gases from the secondary stage reactor showed that the dimethyl ether had been converted completely to methane and carbon oxides and that the overall selectivity to methane based on methanol was 50%.

The sterotex used in this Example is a non-metallic derivative of stearic acid manufactured by the Capital City Product Company, Columbus, Ohio, United States of America.

EXAMPLE 20

The procedure of Example 19 was repeated at an operating pressure of 1200 psia. Similar results were obtained with an overall selectivity to methane based on methanol of 50%.

EXAMPLE 21

The procedure of Example 19 was repeated using a conventional nickel methanation catalyst (Girdler's G.87 methanation catalyst) in place of the HT (high temperature) shift catalyst in the secondary stage reactor. The pressure was again 400 psia and the inlet temperature of both reactors was maintained at 400° C. The gas space velocity (based on methanol) was 2000 $hr^{-1}$. As before, the primary stage reactor converted the methanol to dimethyl ether.

The exit gases from the secondary stage reactor analysed to be 23.66% $CH_4$, 2.04% CO, 11.69% $CO_2$, 47.09%$H_2O$ and 15,51% $H_2$. Calculations show that this analysis corresponds closely to the expected equilibrium position assuming a 100% conversion to dimethyl ether in the primary gasifier and that the gas composition leaving the second reactor was at equilibrium with respect to reactions (3) and (4). No dimethyl ether was detected in the exit gases from the secondary stage reactor.

EXAMPLE 22

The procedure of Example 21 can be repeated using, in separate experiments, ferric tungstate, chromic tungstate. gamma-alumina, ferric phosphate and chromic phosphate respectively in place of aluminium phoshate in the primary stage reactor. Satisfactory results can be obtained in each case.

EXAMPLE 23

The procedure of Example 14 can be repeated with the exception that an experimental fluidised bed reactor is used in place of the experimental reactor used in Examples 1 to 13. Satisfactory results are obtainable.

EXAMPLE 24

The procedure of Example 21 can be repeated using, in place of the pellets of aluminium phosphate, similar sized pellets formed from alumina powder that had been washed with phosphoric acid to convert the surface to aluminium phosphate.

What is claimed is:

1. A catalyst consisting essentially of a major amount of iron oxide, a minor, catalytically-effective amount of chromium oxide sufficient to impart stability to the catalyst, and phosphate or tungstate ions chemically-combined therewith, said phosphate or tungstate ions being present in a minor amount sufficient to impart a dehydration function to the catalyst, said amounts being based on the total weight of said components.

2. A catalyst of claim 1 wherein said chemically-combined ions are phosphate ions.

3. A catalyst of claim 2 wherein said amount of phosphate ions is up to about 9 weight %.

4. A catalyst of claim 2 wherein said amount of chromium is about 4 weight %, calculated as chromium oxide to about 20 weight %.

5. A catalyst of claim 2 wherein said amount of chromium is about 8 weight % calculated as chromium oxide to about 18 weight %.

6. A catalyst of claim 5 wherein said amount of phosphate ions is about 0.5 weight % to about 10 weight %.

7. A catalyst composition of claim 1 having from about 8 to about 18 weight % chromium, calculated as chromium oxide, and from about 1 to about 9 weight % phosphate ions.

8. A catalyst consisting essentially of a major amount of iron oxide, a minor amount of chromium oxide sufficient to impart stability to the catalyst, and phosphate or tungstate ions chemically-combined therewith, said phosphate or tungstate ions being present in a minor amount sufficient to impart a dehydration function to the catalyst, said amounts being based on the total weight of said components, and said catalyst being essentially free from Group 8 metals.

9. A catalyst of claim 8 wherein said chemically-combined ions comprise phosphate ions.

10. A catalyst of claim 9 wherein said amount of phosphate ions is up to about 9 weight %.

11. A catalyst of claim 9 wherein said amount of chromium is about 4 weight % to about 20 weight %, calculated as chromium oxide.

12. A catalyst of claim 11 wherein said amount of chromium is about 8 weight % to about 18 weight %, calculated as chromium oxide.

13. A catalyst of claim 12 wherein said amount of phosphate ions is about 0.5 weight % to about 10 weight %.

14. A catalyst composition of claim 8 having from about 8 to about 18 weight % chromium, calculated as chromium oxide, and from about 1 to about 9 weight % phosphate ions.

* * * * *

UNITED STATES PATENT OFFICE
CERTIFICATE OF CORRECTION

Patent No. 4,021,370    Dated May 3, 1977

Inventor(s) Norman Harris et al.

It is certified that error appears in the above-identified patent and that said Letters Patent are hereby corrected as shown below:

Column 1, line 50 -- the word "he" should be --the--.

Column 3, line 26 -- a percent symbol should appear after the number 4.

Column 4, line 8 -- a closing parenthesis symbol should appear after the word "sulphate".

Column 5, line 5 -- the word --oxide-- should appear after the word "iron".

Column 6, line 55 -- the word before "nickel" should be --as-- instead of "a".

Column 7, line 47 -- the hyphen after the slash needn't be there.

Column 8, line 54 -- 3/16 x 3/16 should be 3/16" x 3/16".

Column 9, line 57 -- there should be a space between the words "inlet" and "and".

Column 11, line 12 -- (Table 2, the second figure in the second column) -- the percentage sign after the number "17.5" should be deleted.

Column 11, line 37 -- the word "trhoughout" should be --throughout".

UNITED STATES PATENT OFFICE
CERTIFICATE OF CORRECTION

Patent No. 4,021,370          Dated May 3, 1977

Inventor(s)  Norman Harris et al.

It is certified that error appears in the above-identified patent and that said Letters Patent are hereby corrected as shown below:

Column 12, line 18 -- the hyphen at the end of the line can be deleted.

Signed and Sealed this

Sixth Day of September 1977

[SEAL]

Attest:

RUTH C. MASON  
Attesting Officer

LUTRELLE F. PARKER  
Acting Commissioner of Patents and Trademarks